(12) United States Patent
Dogac et al.

(10) Patent No.: US 8,321,237 B2
(45) Date of Patent: Nov. 27, 2012

(54) INTEGRATING DIFFERENT PROFILES TO FORM A PROCESS

(75) Inventors: Asuman Dogac, Odtu-Ankara (TR);
Yildiray Kabak, Kucukesat-Ankara (TR); Tuncay Namli, Ankara (TR);
Gokce Banu Laleci Erturkmen, Karakusunlar Ankara (TR)

(73) Assignee: Asuman Dogac, Odtu-Ankara (TR)

( * ) Notice: Subject to any disclaimer, the term of this patent is extended or adjusted under 35 U.S.C. 154(b) by 697 days.

(21) Appl. No.: 12/269,335

(22) Filed: Nov. 12, 2008

(65) Prior Publication Data

US 2010/0122210 A1    May 13, 2010

(51) Int. Cl.
*G06Q 10/00* (2012.01)
(52) U.S. Cl. .............................. 705/2; 705/18
(58) Field of Classification Search ....... 705/2
See application file for complete search history.

(56) References Cited

U.S. PATENT DOCUMENTS

| | | | |
|---|---|---|---|
| 7,475,051 B1* | 1/2009 | Laxminarayan et al. | 706/47 |
| 2008/0208625 A1* | 8/2008 | Joseph | 705/2 |
| 2010/0082369 A1* | 4/2010 | Prenelus et al. | 705/3 |

OTHER PUBLICATIONS

Dogac A., Kabak Y., Namli T., Okcan A.,"Collaborative Business Process Support in eHealth: Integrating IHE Profiles through ebXML Business Process Specification Language", IEEE Transactions on Information Technology in Biomedicine, vol. 12, No. 6, Nov. 2008, pp. 754-762.

* cited by examiner

*Primary Examiner* — Hiep V Nguyen
(74) *Attorney, Agent, or Firm* — Collen IP; Donald J. Ranft

(57) ABSTRACT

In one aspect, a method to integrate different profiles to form a process includes providing to a user a list of actors by profile using a graphical user interface (GUI) of a computer system. An actor includes one of a system or an application stored on a machine-readable medium. The method also includes providing to a user through the GUI a list of transactions by profile performed by the actors, receiving from a user a selection of actors from different profiles to group made by the user using the GUI, receiving from a user definitions of the transactions provided by the user using the GUI, grouping the selection of actors based on at least precedence rules and rendering to the user an integrated profiles graph representing the grouping of the actors from different profiles.

14 Claims, 8 Drawing Sheets

INTEGRATING DIFFERENT PROFILES TO FORM A PROCESS

BACKGROUND

Standards are necessary both for integration and for interoperability. However, any actual implementation of a standard requires some form of tailoring. Therefore, in developing practical and effective interoperability solutions, an industry relies on integration profiles which are business processes describing selected real-world use-cases. One important industry initiative, Integrating Healthcare Enterprise (IHE), has taken this profiling approach to achieve interoperability in the eHealth domain.

IHE is a not-for-profit initiative founded by the Radiological Society of North America (RSNA) and the Healthcare Information and Management Systems Society (HIMSS) and is supported by a wide range of healthcare professional societies world-wide. Through the IHE Profiles, the interactions between the IT systems in healthcare are described and the details of interfaces are fixed based on the standards. The approach taken in developing the integration profiles is first to define the basic transactions describing the interactions between the IT systems and then to define the workflows describing the real-life business processes by using these transactions together with the standard interfaces. Since IHE Profiles describe the specific use cases, there is a need to combine more than one IHE Profile to achieve the required functionality in realizing a real-world scenario. For example, one profile, called an IHE Cross-Enterprise Document Sharing (IHE-XDS) Profile, specifies how patient clinical data can be shared among different healthcare enterprises and allows Electronic Healthcare Records (EHRs) to be shared through a common ebXML Registry/Repository architecture. Another profile, called a Patient Identifier Cross-referencing Integration (IHE-PIX) Profile, specifies how patient identifiers used in different healthcare institutes should be mapped to each other and supports the cross-referencing of patient identifiers from multiple patient identifier domains.

SUMMARY

In one aspect, a method to integrate different profiles to form a process includes providing to a user a list of actors by profile using a graphical user interface (GUI) of a computer system. An actor includes one of a system or an application stored on a machine-readable medium. The method also includes providing to a user through the GUI a list of transactions by profile performed by the actors, receiving from a user a selection of actors from different profiles to group made by the user using the GUI, receiving from a user definitions of the transactions provided by the user using the GUI, grouping the selection of actors based on at least precedence rules and rendering to the user an integrated profiles graph representing the grouping of the actors from different profiles.

In another aspect, an article includes a machine-readable medium that stores executable instructions to integrate different profiles to form a process. The instructions cause a machine to provide to a user a list of actors by profile using a graphical user interface (GUI) of a computer system. An actor includes one of a system or an application. The instructions also cause the machine to provide to a user through the GUI a list of transactions by profile performed by the actors, receive from a user a selection of actors from different profiles to group made by the user using the GUI, receive from a user definitions of the transactions provided by the user using the GUI, group the selection of actors based on at least precedence rules and render to the user an integrated profiles graph representing the grouping of the actors from different profiles.

In a further aspect, an apparatus to integrate different profiles to form a process includes circuitry to provide to a user a list of actors by profile using a graphical user interface (GUI) of a computer system. An actor includes one of a system or an application. The apparatus also includes circuitry to provide to a user through the GUI a list of transactions by profile performed by the actors, receive from a user a selection of actors from different profiles to group made by the user using the GUI, receive from a user definitions of the transactions provided by the user using the GUI, group the selection of actors based on at least precedence rules and render to the user an integrated profiles graph representing the grouping of the actors from different profiles.

DETAILED DESCRIPTION

Figure 1:
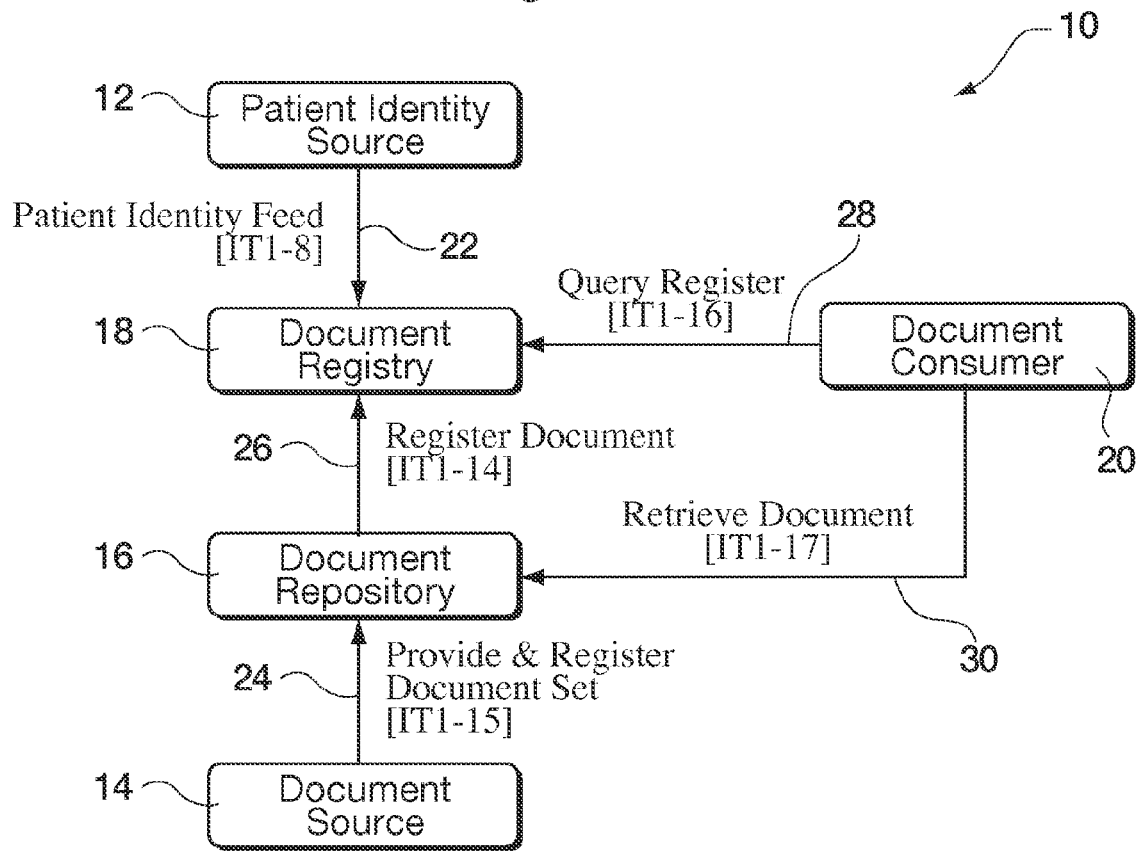
FIG. 1 is a diagram of a profile for an Integrating Healthcare Enterprise (IHE) Cross-Enterprise Document Sharing (IHE-XDS).

The ability to share patient data formed by different applications through an IHE Cross-Enterprise Document Sharing (IHE-XDS) profile, for example, requires mapping patient identifiers used by these other applications to each other. Therefore, it is desirable to use the IHE-XDS Profile together with a Patient Identifier Cross-referencing Integration (IHE-PIX) Profile, for example. IHE provides for this by grouping the relevant actors of the involved profiles manually. When IHE Profiles are combined by grouping relevant IHE Actors, the result is a collaborative healthcare business process integrating the workflows defined for each profile and the sequence of the transactions coming from different profiles must be decided.

Given the large number of Integrating Healthcare Enterprise (IHE) Profiles (currently over sixty profiles), determining a precedence of all the transactions involved manually for each possible combination of the profiles is a very a tedious task. For example, each user or vendor may support a different set of IHE Profiles from which to choose; and hence, the overall business process for each user or vendor may be different. And secondly, the overall business process must be described in a machine-processable way to be used by the collaborating applications. Described herein is a process to obtain the overall machine-processable multi-party collaborative business process automatically when IHE Actors are grouped.

For this purpose, IHE Profiles in OASIS ebXML Business Process Specification Language are described herein. It is shown that by representing the IHE Profiles through directed graphs and by using the rules giving the precedence information among the IHE Transactions, it is possible to automatically order the transactions in the overall business process when the Actors are grouped so that a graphical tool may be provide based on this mechanism to produce an overall business process automatically when a user selects the IHE Actors to be grouped.

The eBusiness eXtensible Markup Language (ebXML) Business Process Specification Schema (ebBP) technical specification defines a standard, machine-processable language by which business systems may be configured. A Business Collaboration consists of a set of roles that collaborate by exchanging Business Documents. The roles and the documents they exchange are defined in Business Transactions. The roles in Business Transactions are generic and labeled as Requesting and Responding roles. When a Business Transaction definition is used for a specific purpose in a Business Collaboration, it becomes a Business Transaction Activity. The specific roles (e.g. Document Source, Document Consumer) are specified at the Business Transaction Activity level. Similarly when Business Collaborations are used for a specific purpose, they are termed as a Collaboration Activity. A Business Collaboration is defined as a choreography of Business Transaction Activities and/or Collaboration Activities. The purpose of the choreography is to specify which Business Transaction Activity and/or Collaboration Activity should occur. There are a number of States that facilitate the choreographing of Business Activities. These include a Start State and a Completion State (which is either a Success or a Failure) as well as a series of gateways: a Fork gateway, a Join gateway and a Decision gateway. There are two types of Fork gateways: "OR" and "XOR."

The ebBP defines a Business Transaction as an abstract entity and provides concrete business patterns to be used in real-life business collaborations. Each of the concrete business patterns describes whether a response document is required and which business signals are required in a specific interaction. The concrete business patterns include a Commercial Transaction, a Notification, an Information Distribution, a Query/Response, a Request/Response and a Request/Confirm.

The Commercial Transaction (previously represented as a Business Transaction) is a pattern that defines a formal obligation between parties and requires a response, a request receipt acknowledgement and a response receipt acknowledgement or an exception. The Notification is a pattern that is used for business notifications such as a Notification of Failure and it does not require a response document. The Information Distribution is a pattern that represents an informal information exchange between parties. The Query/Response is a pattern that is used by a requester for an information query of which the responding party already has. In this pattern, on the receiver side there is no backend processing; otherwise the Request/Response pattern should be used. The Request/Response is a pattern that is used when an initiating party requests information that a responding party already has and when the request for business information requires a complex interdependent set of results and backend processing. The Request/Confirm is a pattern that is used when an initiating party requests confirmation about its status with respect to previous obligations or a responder's business rules.

IHE Integration Profiles are business processes describing selected real-world use-cases. Each IT system or application (e.g., stored on a machine-readable medium) involved in the use cases is called an Actor. The interactions between IHE Actors are defined through Transactions. More specifically, IHE Transactions define how IT systems or applications communicate by using existing standards such as Health Level Seven (HL7) or Digital Imaging and Communications in Medicine (DICOM) to accomplish a specific task. In this way, IHE Integration Profiles define a collection of business processes. Currently, there are about sixty IHE Profiles addressing different use cases in the healthcare IT domain including how to share patient clinical information (IHE-XDS), how to map patient identifiers from one domain into another (IHE-PIX) and how to provide authentication and audit trail (IHE-ATNA). IHE continuously defines more profiles to address the remaining integration issues in the healthcare IT domain.

In an IHE Cross-Enterprise Document Sharing (XDS) Profile, the repository is used for storing the clinical documents and the related metadata stored at the registry is used to facilitate the discovery of the documents. In this profile, the group of healthcare enterprises that agree to work together for clinical document sharing is called an XDS Affinity Domain. Such enterprises agree on a common set of policies such as how the consent is obtained, the access is controlled, and the common set of coding terms to represent the metadata of the documents. The metadata defined is used for searching the registry to locate the documents in the repository.

Referring to FIG. 1, an IHE XDS Profile 10 includes actors that are linked together by transactions. The actors include a Patient Identity Source Actor 12, a Document Source Actor 14, a Document Repository Actor 16, a Document Registry Actor 18 and a Document Consumer Actor 20. The transactions include a Patient Identity Feed (IHE-ITI-8) Transaction 22, a Register Document Set (IHE-ITI-15) Transaction 24, a Register Document Set (IHE ITI-14) Transaction 26, a Query Registry (IHE-ITI-16) Transaction 28, and a Retrieve Document (IHE-ITI-17) Transaction 30.

The Patient Identity Source Actor 12 provides a patient identifier to the Document Registry Actor 22 using the Patient Identity Feed (IHE-ITI-8) Transaction 22. The Document Source Actor 14, by using the Provide and Register Document Set (IHE-ITI 15) Transaction 24, sends documents to the Document Repository Actor 16. The Document Repository Actor 16 stores the documents at a persistent storage and sends metadata of the documents to appropriate the Document Registry Actor 18 by using the Register Document Set (IHE ITI-14) Transaction 26. The Document Registry Actor 18 maintains metadata about each registered document in a document entry, which includes a link to the document in the Repository where it is stored. The Document Consumer Actor 20 queries a Document Registry Actor 22 for documents meeting certain criteria on metadata by using the Query Registry (IHE-ITI 16) Transaction 28, and retrieves selected documents from one or more Document Repository Actors 16 through the Retrieve Document (IHE-ITI 17) Transaction 30.

ebBP defines generic business transaction patterns and specifies how to organize them into business processes in a standard and machine-processable way. IHE Profiles, on the other hand, define healthcare domain specific business transactions and specify some of the business processes in the healthcare domain. The main advantage of representing IHE Profiles through ebBP is that, in this way IHE Profiles become machine-processable in a standard way and this in turn introduces a new ability to combine various healthcare processes automatically.

The correspondence between the ebBP concepts and the IHE concepts are shown in Table I:

TABLE I

THE CORRESPONDANCE OF IHE CONCEPTS TO ebBP CONCEPTS

| IHE Concepts | ebBP Concepts |
|---|---|
| IHE Actor | ebBP Role |
| IHE Transaction (generic) | ebBP Business Transaction |
| IHE Transaction (specific to a Profile) | ebBP Business Collaboration |
| IHE Message, Document | ebBP Business Document |
| IHE Sequence Diagram | ebBP Choreography |
| IHE Profile | ebBP Business Process |

IHE Actors correspond to ebBP Roles. A generic IHE Transaction, that is, an IHE Transaction that is not bound to an IHE Profile yet, is represented through ebBP Business Transaction. When an IHE Transaction is bound to an IHE Profile through a Business Collaboration, a concrete Requesting Role and a Responding Role as well as the choreography of the transactions are determined. IHE messages and documents used in a Business Transaction correspond to ebBP Business Documents. IHE Profile Sequence Diagrams determine the choreography of the related Business Collaboration.

The following steps are involved in representing the IHE Profiles in ebBP. First, the IHE transactions are mapped to the ebBP transaction patterns. As shown in Table I, ebBP defines six concrete business transaction patterns with well defined semantics and how to represent the IHE Transactions through the ebBP Transaction patterns.

Second, once IHE Transactions are defined through ebBP, they are tailored to IHE Business Collaborations. When an IHE Transaction is bound to an IHE Profile through a Business Collaboration, the concrete Requesting Role and the Responding Role as well as the choreography of the transactions are determined. For example, the generic Patient Identity Feed (IHE-ITI-2) Transaction between two generic roles such as a Patient Identity Supplier and a Patient Identity Receiver can be specialized to a Patient Identity Feed Transaction in IHE XDS or to a Patient Identity Feed Transaction in IHE PIX by setting the concrete roles accordingly, that is, for the PIX Profile the Patient Identity Receiver is set to the PIX Manager Actor; for the XDS Profile it is set to the Document Registry Actor.

Third, the related Business Collaborations are combined to make up the IHE Profile. At this step, it may be necessary to introduce new business collaborations by using the previously defined Business Collaborations to be able to express further interactions among them.

ebBP patterns describe certain generic semantics. For example, the Commercial Transaction (also termed as the Business Transaction) defines a formal obligation between parties and requires a response, a request receipt acknowledgement and a response receipt acknowledgement or an exception. This pattern matches with the semantics of the Provide/Register Document Set (IHE-ITI-15) Transaction 24 semantics. As another example, the IHE Query Registry (IHE-ITI-16) 28 Transaction is a specialization of the ebBP Query/Response Transaction Pattern since the Document Consumer 20 is in need of information that the Registry may have.

In Table II, the correspondences between IHE-XDS Transactions and ebBP patterns are given.

TABLE II

CORRESPONDENCE OF IHE XDS TRANSACTIONS TO ebBP BUSINESS TRANSACTION PATTERNS

| IHE Transaction | ebBP Pattern | Requesting Role | Responding Role | Business Document |
|---|---|---|---|---|
| Provide/Register Document Set | Business Transaction | Document Source | Document Repository | Document, Document Metadata |
| Query Registry | Query/Response | Document Consumer | Document Registry | XDS Query |
| Retrieve Document | Request/Response | Document Consumer | Document Repository | URI |
| Register Document Set | Request/Confirm | Document Repository | Document Registry | Document Metadata, Document Metadata Ack. |
| Admit/Register or Update Patient (Patient Identity Feed) | Information Distribution | Patient Identity Source | Document Registry, Patient Identity Cross-reference Manager | HL7 ADT A01/A04/A05 |

An IHE Transaction can be represented through ebBP. For example, the Patient Identity Feed (IHE-ITI-8) Transaction 22 communicates patient information, including corroborating demographic data, after a patients identity is established, modified or merged.

Figure 2:
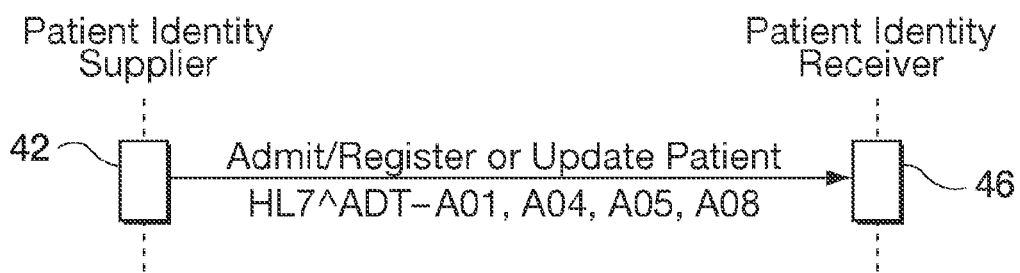
FIG. 2 is a diagram of a Patient Identity Feed Transaction (IHE-ITI-8) Sequence Diagram.

Referring to FIG. 2, an IHE Sequence Diagram 40 for the Patient Identity Feed (IHE-ITI-8) Transaction 22 is shown. A Patient Identity Supplier Actor 42 provides a patient identifier to a Patient Identity Receiver Actor 46 when an event occurs (e.g., a creation, an update or a merge). The messages used for this purpose are, for example, HL7 Admit Patient (ADT) messages such as A01 for admission of an in-patient into a facility or A04 for registration of an outpatient for a visit of the facility.

The following is a code listing of the IHE Patient Identity Feed transaction 22 in ebBP:

<Notification nameID="IHE-ITI-8" name="Patient IdentityFeed Business Transaction" isGuaranteedDeliveryRequired="true">

-continued

```
<RequestingRole nameID="PIDFeedBT-Initiator"
   name="Initiator"/>
<RespondingRole nameID="PIDFeedBT-Responder"
   name="Responder"/>
<RequestingBusinessActivity
   nameID="PIDFeedBT-RBA"
   name="Patient Identity Feed Requesting Business
   Activity" isAuthorizationRequired="true"
   isNonRepudiationRequired="true">
   <DocumentEnvelope
      nameID="HL7-v2.3.1-ADT"
      businessDocumentRef="HL7-2.3.1-ADT-Document"
      name="HL7 v2.3.1 ADT Message"
      isAuthenticated="persistent"
      isConfidential="persistent"/>
   <ReceiptAcknowledgement name="ra2" nameID=
      "PIDFeedBT-RBA-RA" signalDefinitionRef="ra2"/>
   <ReceiptAcknowledgementException name="rae2" nameID=
      "PIDFeedBT-RBA-RAE" signalDefinitionRef="rae2"/>
   <AcceptanceAcknowledgement name="aa2" nameID=
      "PIDFeedBT-RBA-AA" signalDefinitionRef="aa2"/>
   <AcceptanceAcknowledgementException name="aae2"
      nameID="PIDFeedBT-RBA-AAE" signalDefinitionRef=
      "aae2"/>
</RequestingBusinessActivity>
<RespondingBusinessActivity nameID="PIDFeedBT-ResBA"
   name="Patient Identity Feed Responding Business
   Activity">
</RespondingBusinessActivity>
</Notification>
```

The IHE Patient Identity Feed transaction 22 in ebBP is a specialization of ebBP Notification pattern since it does not require a response. It defines a generic Requesting Role and a Responding Role as a PID Feed BT-Initiator and a PID Feed BT Responder respectively. A Requesting Business Activity defines the business document reference as aHL7-2.3.1-ADTDocument. Furthermore, the necessary signals for state alignment are defined.

An IHE Business Collaboration is obtained by tailoring a generic IHE Transaction to a specific IHE Profile. Furthermore, the choreography (the ordering and transitions between Business Transactions) of the collaboration is described through ebBP standard choreography constructs such as Start, Transition, To Link and From Link. For example, the IHE Patient Identity Feed Transaction 22 is specialized to the IHE PIX Profile by setting the PID Feed BT Initiator role defined in a Patient Identity Feed Transaction (in the code listing of the IHE Patient Identity Feed transaction 22 in ebBP) to a PID Source and a PID Feed BT-Responder role to a PIX Manager. Furthermore, the collaboration references the Patient Identity Feed Transaction (IHE-ITI-8) through a business Transaction Ref element.

As previously described, the choreography of the collaboration is described through ebBP standard choreography constructs. For example, after a start state, a link to the PID Feed BTA activity is specified and the transitions from this state to the two possible states (Success and Failure) are stated. A failure state is omitted from the code listing for the sake of simplicity.

In defining the IHE Profiles through ebBP, previously defined collaborations are reused and new collaborations are introduced as needed. For example, in IHE XDS there are collaborations among the Document Source, the Document Repository 16 and the Document Registry 18 Actors: when a Document Repository Actor 16 receives a Document set from the Document Source Actor 14, it stores this document set at the persistent storage and sends its metadata to the appropriate Document Registry Actor 18 by using the IHE Register Document Set Transaction. In order to express the choreography between three IHE Actors, it is necessary to introduce a new business collaboration by using the previously defined Business Collaborations between two IHE Actors and it is expressed as:

```
<BusinessCollaboration name="Collaboration of IHE
   ITI 14 and IHE ITI 15" nameID="IHE-ITI-14-15">
   <Role name="Document Source" nameID=
      "ITI14-15-XDSSource"/>
   <Role name="Document Repository" nameID=
      "ITI14-15-XDSRepository"/>
   <Role name="Document Registry" nameID=
      "ITI14-15-XDSRegistry"/>
   <TimeToPerform/>
   <Start>
      <ToLink toBusinessStateRef="CA-IHE-ITI-15"/>
   </Start>
   <CollaborationActivity name="IHE ITI 15" nameID
      ="CA-IHE-ITI-15" collaborationRef="XDS-IHE-ITI-15">
      <Performs currentRoleRef="ITI14-15-XDSSource"
         performsRoleRef="PRDSXDSSource"/>
      <Performs currentRoleRef="ITI14-15-XDSRepository"
         performsRoleRef="PRDSXDSRepository"/>
   </CollaborationActivity>
   <Transition>
      <FromLink fromBusinessStateRef="CA-IHE-ITI-15"/>
      <ToLink toBusinessStateRef="CA-IHE-ITI-14"/>
   </Transition>
   <CollaborationActivity name="IHE ITI 14" nameID=
      "CA-IHE-ITI-14" collaborationRef="XDS-IHE-ITI-14">
      <Performs currentRoleRef="ITI14-15-XDSRepository"
         performsRoleRef="RDSXDSRepository"/>
      <Performs currentRoleRef="ITI14-15-XDSRegistry"
         performsRoleRef="RDSXDSRegistry"/>
   </CollaborationActivity>
   <Transition>
      <FromLink fromBusinessStateRef="CA-IHE-ITI-14"/>
      <ToLink toBusinessStateRef="ITI14-15-Success"/>
   </Transition>
   <Success name="Success" nameID="ITI14-15-Success"/>
</BusinessCollaboration>
```

The previously defined Business Collaborations between two IHE Actors, that is XDS-IHE-ITI-15 and XDS-IHE-ITI-14 transactions are re-used by providing collaboration references to them and the additional choreography is defined by stating the transitions, first from CA-IHE-ITI-15 to CA-IHE-ITI-14, and then from CA-IHE-ITI-14 to ITI14-15-Success. A failure state is omitted from the code listing for the sake of simplicity.

There is a need to automatically generate custom design business processes, integrating any possible existing or forthcoming IHE profiles according to user needs. A software tool may be used to order transactions automatically for the grouped IHE Actors, called an IHE Actor Grouping Tool (IHE-AGT). The IHE-AGT tool is based on the algorithm described. The notations and the data structures used in the algorithm are given in Table III and Table IV, respectively.

TABLE III

NOTATIONS USED IN THE ALGORITHM

| Notation | Description |
| --- | --- |
| $A = \{a_1, a_2, \ldots, a_n\}$ | List of actors in the profile |
| $T = \{t_1, t_2, \ldots, t_m\}$ | List of transactions in the profile |
| $G = \{g_1, g_2, \ldots, g_l\}$ | List of graphs in the profile |
| $PR = \{pr_1, pr_2, \ldots, pr_k\}$ | List of profile rules |
| $GR = \{gr_1, gr_2, \ldots, gr_j\}$ | List of grouping rules |

TABLE IV

DATA STRUCTURES USED IN THE ALGORITHM

| Structure | Description |
|---|---|
| $t_i$ | Each transaction is a quadruple <name, initiator, responder, seqnum> name is the name of the xAnct, initiator is the initiator actor, responder is the responder actor, Seqnum shows the sequence number of the transaction in a collaboration. It is initially set to 1. |
| $g_i$ | Each graph is a two-dimensional N × N array (i.e. matrix) whose elements point to a transaction list. The indices (i.e. vertices) of the graph are actors. The entries in the graph are a list of transactions (i.e. edges). |
| $pr_i$ | Each profile rule is a list of transactions. The sequence of the transactions shows their expected order in the profile. |
| $gr_i$ | Each grouping rule is a tuple of the form <left, right>. left: is a tuple of actors right: is a tuple of xAncts of the form <first precedes next>. This means, if actors in left are grouped, then first must precede next. |

The first requirement for automation is to have a machine-processable definition of IHE Profiles by defining IHE Profiles through ebBP. The next step is to be able to decide on the execution sequence of transactions coming from different profiles.

To automate this process, use is made of the precedence rules in the IHE Profiles. There are two types of precedence rules. First, there is a precedence among transactions within an IHE Profile, which called Profile Precedence rules. For example, in IHE XDS, the transaction XDS-ITI-15 XDS Provide/Register Document Set must precede the transaction XDS-ITI-14 XDS Register Document Set. Second, when two Actors from different profiles are grouped, there is a precedence among their transactions, which is called Grouping Precedence rules. For example, in IHE XDS, there is a need for node authentication and for an audit trail to provide patient information confidentiality and user accountability. To achieve this, IHE Audit Trail and Node Authentication (ATNA) Integration Profile is used together with IHE XDS. To make these two profiles work together, ATNA Secure Node Actor is grouped with each of the following IHE-XDS Actors: XDS Document Source 14, XDS Document Repository 16, XDS Document Registry 18 and XDS Document Consumer 20.

Figure 3:
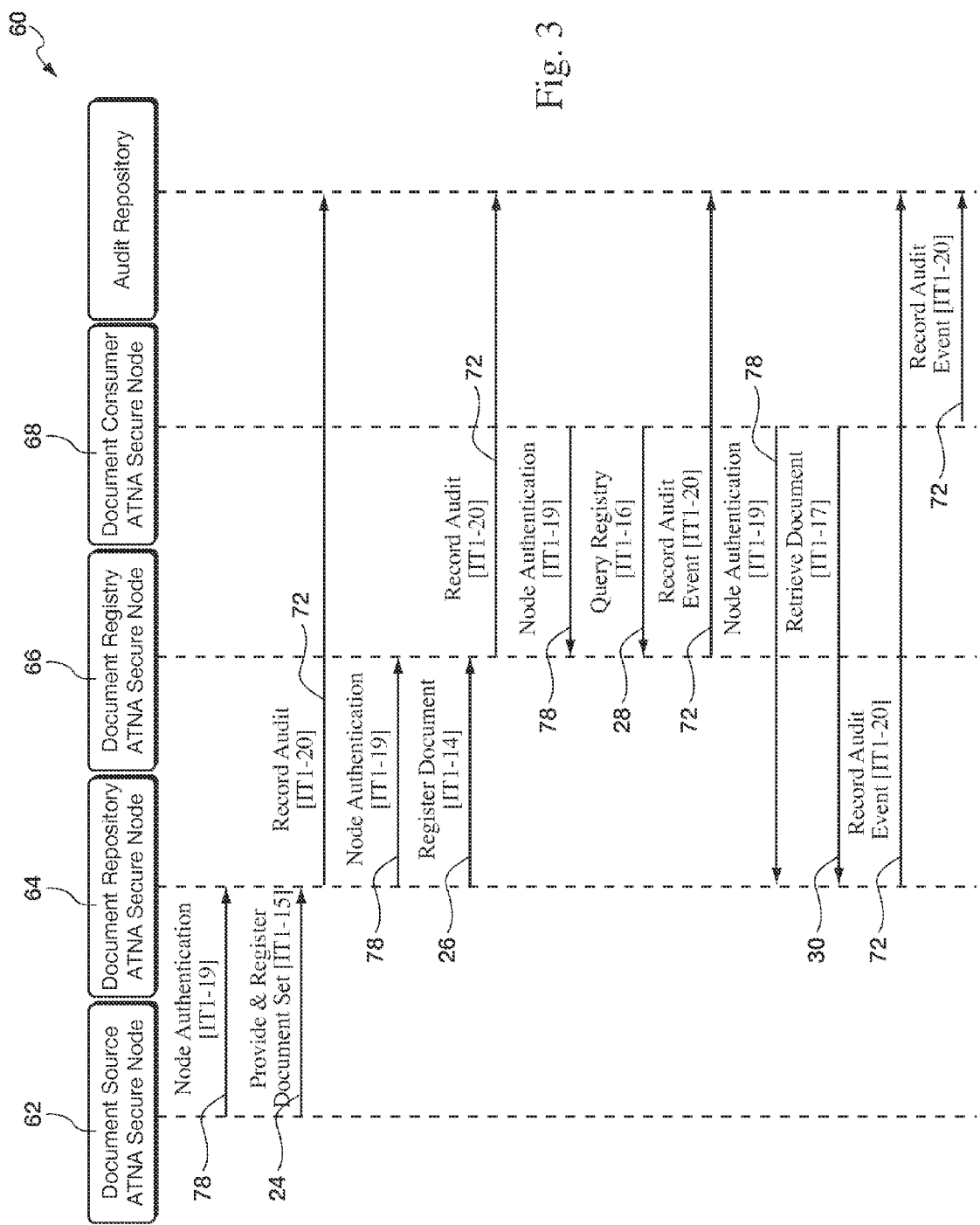
FIG. 3 is a sequence diagram depicting an ordering of transactions after combining IHE-XDS and IHE ATNA profiles.

Referring to FIG. 3, a resulting sequence 60 of transactions is a result of these Actors being grouped. The sequence 60 includes a Document Source ATNA Secured Node 62, a Document Repository ATNA Secure Node 64, a Document Registry ATNA Secure Node 66 and a Document Consumer ATNA Secure Node 68. The transactions include a record audit event (IHE-ITI-20) transaction 72, a retrieve document (IHE-ITI-17) transaction 30, a provide/register (IHE-ITI-15) transaction 24, a register document set (IHE-ITI-14) transaction 26, a node authentication transaction (IHE-ITI-19) transaction 78 and a query registry (IHE-ITI-16) transaction 28.

For example, the record audit event (IHE-ITI-20) transaction 72 of ATNA is inserted between the provide/register document set (IHE-ITI-15) transaction 74 and the register document set (IHE-ITI-14) transaction 76.

For expressing these precedence rules, the following notation was developed:

<InitiatingActor1, RespondingActor1, "IHE-Transaction1"> precedes <InitiatingActor2, RespondingActor2, "IHE-Transaction2">,
which indicates that the "IHE-Transaction1" between InitiatingActor1, and RespondingActor1 precedes "IHE-Transaction2" between InitiatingActor2 and RespondingActor2.

One example of a precedence rule among the transactions within the IHE XDS Profile is:

{hXDSDocumentSource, XDSDocumentRepository, XDS-ITI-15i precedes hXDSDocumentRepository, XDSDocumentRegistry, XDS-ITI-14i}.

Another example of a precedence rule among the transactions within the IHE XDS Profile is:

{hXDSDocumentConsumer, XDSDocumentRegistry, XDS-ITI-16i precedes hXDSDocumentConsumer, XDSDocumentRepository, XDS-ITI-17i}.

Some example rules for grouping Actors across IHE Profiles are listed below:
1. [hXDSDocumentSource, ATNASecureNodei, hhXDSDocumentSource, XDSDocumentRepository, ATNA-ITI-19i precedes hXDSDocumentSource, XDSDocumentRepository, XDS-ITI-15ii]
2. [hXDSDocumentRepository, ATNASecureNodei, hhXDSDocumentSource, XDSDocumentRepository, XDS-ITI-15i precedes hXDSDocumentRepository, AuditRepository, ATNA-ITI-20ii]
3. [hXDSDocumentRepository, ATNASecureNodei, hhXDSDocumentRepository, XDSDocumentRegistry, ATNA-ITI-19i precedes hXDSDocumentRepository, XDSDocumentRegistry, XDS-ITI-14ii]
4. [hXDSDocumentRegistry, ATNASecureNodei, hhXDSDocumentRepository, XDSDocumentRegistry, XDS-ITI-14i precedes hXDSDocumentRegistry, AuditRepository, ATNA-ITI-20ii]
5. [hXDSDocumentRegistry, ATNASecureNodei, hhXDSDocumentConsumer, XDSDocumentRegistry, XDS-ITI-16i precedes hXDSDocumentRegistry, AuditRepository, ATNA-ITI-20ii]
6. [hXDSDocumentConsumer, ATNASecureNodei, hhXDSDocumentConsumer, XDSDocumentRegistry, ATNA-ITI-19i precedes hXDSDocumentConsumer, XDSDocumentRegistry, XDS-ITI-16ii]

To automate processing, the precedence rules are expressed in the Rule Markup Language (RuleML). An actor grouping process 100 is a graph-based process where each profile is represented as a directed graph. In the graph, the vertices are the IHE actors and the edges are the IHE transactions. A directed edge between two vertices shows a transaction whose initiator actor is the source vertex and responder actor is target vertex. In the process 100, the graphs are represented with two-dimensional N×N arrays whose elements point to a list of transactions. The vertices or nodes in the graph (representing the actors) are represented by the indices of the array and the edges (representing the transactions) are represented by the entries of the array. For example, g[a1][a2] returns a transaction list (from actor a1 to actor a2) which shows the edges from vertex a1 to vertex a2. The algorithm receives three types of input: (1) a list of actors, (2) a list of transactions and (3) precedence rules for the IHE Profiles.

The process 100 includes three phases: a construction phase 104, a partitioning phase 108 and a merging phase 112. In the construction phase 104, the transaction list is iterated and each transaction is added to the graph by assigning its label indicating its execution order (termed as "a sequence number" in the algorithm). For assigning the sequence numbers, the precedence rules are used. At the end of the construction phase 104, an overall profile graph (e.g., a profile graph 200 (FIG. 5A)) is produced.

Figure 5A:
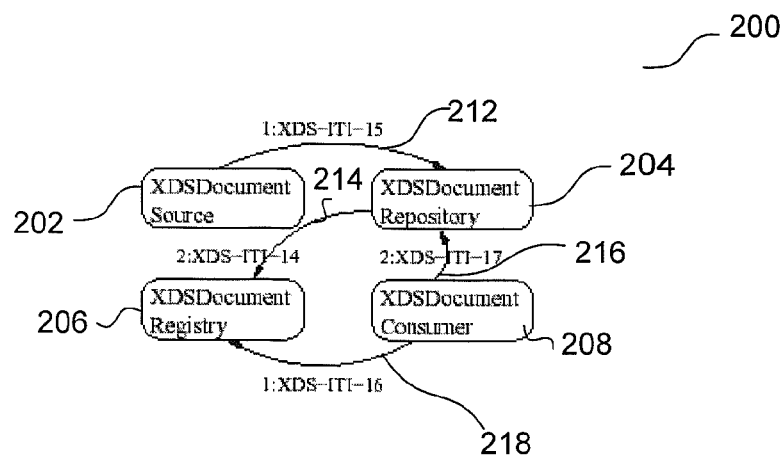
FIG. 5A is a profile graph representing the IHE-XDS profile.

Referring to FIG. 5A, in an example using the IHE XDS Profile, a directed graph 200 is an output of the construction phase 104. The graph 200 includes an XDS Document source actor 202, an XDS Document repository actor 204, an XDS Document registry actor 206 and an XDS Document consumer actor 208. The XDS Document source actor 202 provides information to the XDS Document repository actor 204 through an XDS-ITI-15 transaction 212. The XDS Document repository actor 204 provides information to the XDS Document registry actor 206 through an XDS-ITI-14 transaction 214. The XDS Document consumer actor 208 provides information to the XDS Document registry actor 206 through an XDS-ITI-16 transaction 218 and provides information to XDS Document repository actor 204 through an XDS-ITI-16 transaction 218. The XDS-ITI-15 transaction 212 and the XDS-ITI-16 transaction 218 each have a sequence number "1" and the XDS-ITI-14 transaction 214 and the XDS-ITI-17 transaction 216 each have the sequence number "2" indicating their execution order (e.g., a transaction with a "1" occurs before a transaction with a "2"). In terms of notation inn FIGS. 5A-5C and FIGS. 6A-6B, a sequence number precedes the transaction name. For example, in FIGS. 5A-5C, "1 :XDS-ITI-15" represents that the XDS-ITI-15 transaction 212 has a sequence number of "1," "2: XDS-ITI-14" represents that the XDS-IT-14 transaction 214 has a sequence number of "2," "1 :XDS-ITI-16" represents that the XDS-ITI-16 transaction 218 has a sequence number of "1" and "2: XDS-ITI-17" represents that the XDS-IT-17 transaction 216 has a sequence number of "2."

Once the profile graph 200 is constructed, connected subcomponents of the graph 200 are formed in the partitioning phase 108. In other words, the graph 200 is split into subgraphs (e.g., subgraphs 240 and 270) each of which is a distinct business collaboration among IHE actors in order to determine the transactions whose sequences depend on each other.

Figure 5B:
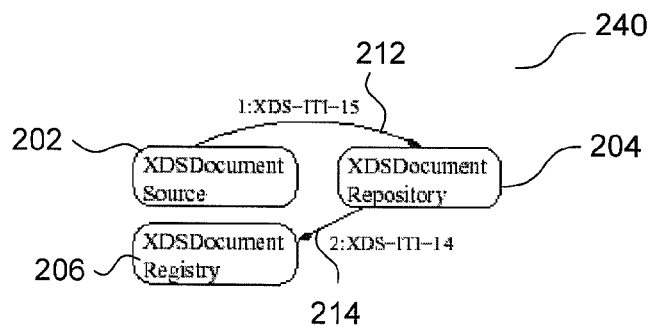
FIGS. 5B and 5C are subgraphs of the profile graph in FIG. 5A.
Figure 5C:
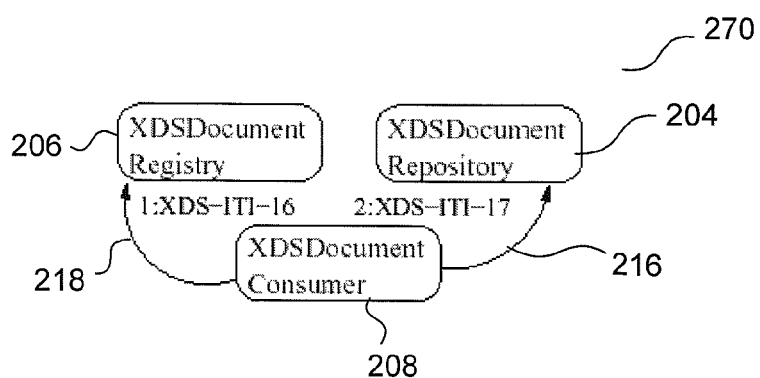

For example, the subgraph 240 in FIG. 5B includes the XDS Document source actor 202 as a starting node connected to the XDS Document repository actor 204 by the XDS-ITI-15 transaction 212 and the XDS Document repository actor 204 is connected to the XDS Document Registry 206 by the XDS-ITI-14 transaction 214. The subgraph 270 in FIG. 5C includes the XDS Document Consumer actor 208 as a starting node connected to the XDS Document repository actor by the XDS-ITI-17 transaction 216 and connected to the XDS Document registry actor 206 by the XDS-ITI-16 transaction 218.

In one example, the partitioning phase produces a set of subgraphs, called G. In the merging phase 112, the precedence rules for grouping are applied to each subgraph in G. In one example, a merging algorithm applied in the merging phase 112 is:

```
1.  for all g ∈ G do begin
2.     for all gr ∈ GR do begin
3.        firstXanct = gr.right.first;
4.        nextXanct = gr.right.next;
5.        // if the graph contains the first transaction
6.        if(g.contains(firstXanct)) do begin
7.           // indexOf function returns the seqnum of the specified transaction in the graph
8.           index = g.indexOf(firstXanct);
9.           if(firstXanct.initiator == nextXanct.initiator and firstXanct.responder ==
              nextXanct.responder)
10.          do begin
11.             edgeList = g[firstXanct.initiator][firstXanct.responder];
12.             edgeList.add(nextXanct);
13.          else
14.             g.addColumn(nextXanct.responder);
15.             g.addRow(nextXanct.responder);
16.             g[nextXanct.initiator][nextXanct.responder].add(nextXanct);
17.          end
18.          // updateIndicesInGraph function increases the seqnum of all transactions
19.          // whose seqnums are greater than or equal to second argument by one
20.          updateIndicesInGraph(g, index+1);
21.          nextXanct.seqnum = index+1;
22.       else
23.          index = g.indexOf(nextXanct);
24.          if(nextXanct.initiator == firstXanct.initiator and
             nextXanct.responder == firstXanct.responder)
25.          do begin
26.             edgeList = g[nextXanct.initiator][nextXanct.responder];
27.             edgeList.add(firstXanct);
28.          else
29.             // addColumn function adds a new column to the graph if there is not.
30.             g.addColumn(firstXanct.responder);
31.             // addRow function adds a new row to the graph if there is not such a row.
32.             g.addRow(firstXanct.responder);
33.             g[firstXanct.initiator][firstXanct.responder].add(firstXanct);
34.          end
35.          updateIndicesInGraph(g, index);
36.          firstXanct.seqnum = index;
```

```
37.    end
38.    end
39end
```

The merging algorithm incorporates the missing transactions in the rules to the graph. For example, assume the following rule exists in GR (Table III):

<<a1, a2> precedes <t1, t2>>, which means that if a1 is grouped with a2, then, in the process, t1 should precede t2. Assume further that a1 already exists in the graph. Then, the merging algorithm adds a2 to the graph and adjusts the sequence numbers of the transactions accordingly. A transaction existence check is performed at Line 6 of the algorithm and the sequence numbers are adjusted at Lines 20-21 and 35-36. For example, in the merging phase 112, when inserting the transactions specified in the grouping rules to the subgraphs, the existence of the transactions are checked.

Figure 6A:
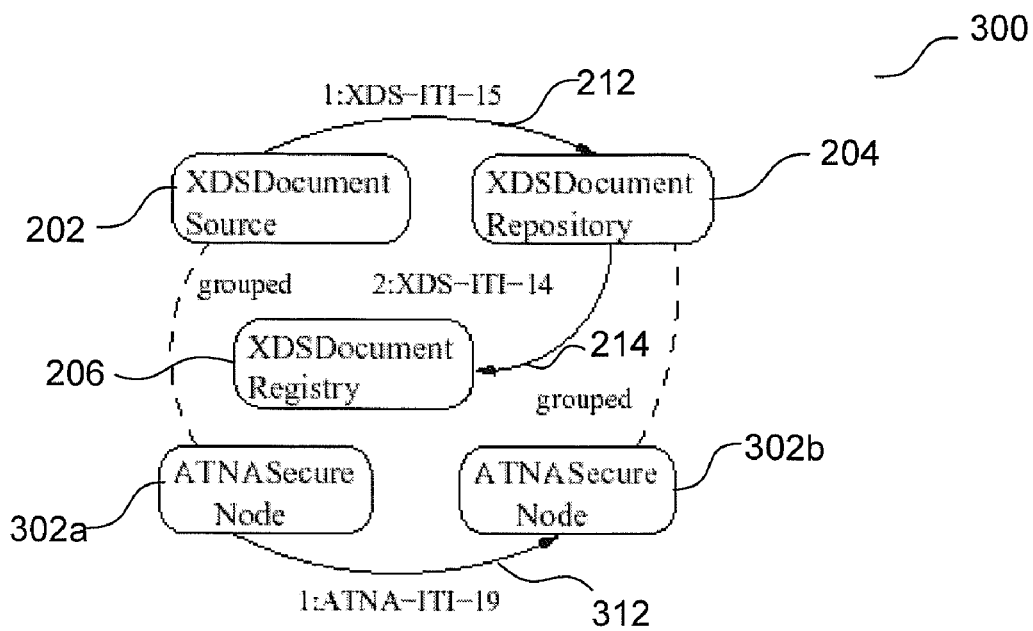
FIG. 6A is an example of a graph prior to merging IHE actors.
Figure 6B:
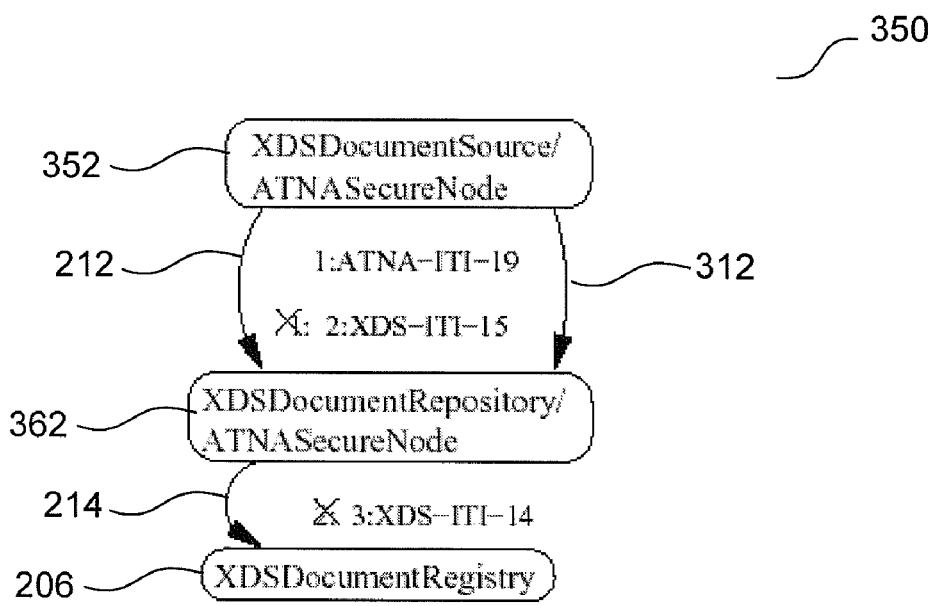
FIG. 6B is an example of an integrated profiles graph after merging the IHE actors.

Referring to FIGS. 6A and 6B and continuing with the previous example, a graph 300 representing unmerged actors is used to form an integrated profiles graph 350. In particular, the XDS Document Source actor 202 is grouped with an ATNA Secure Node 302a and the XDS Document Repository 204 is grouped with an ATNA Secure Node 302b. The XDS Document Source 202 and ATNA Secure Node 302a are merged to form an XDS Document Source/ATNA Secure Node 352 and the XDS Document Repository 204 is merged with the ATNA Secure Node 302b to form the XDS Document Repository/ATNA Secure Node 362. From a rule: 'When "XDS Document Source" is grouped with "ATNA Secure Node," <XDS Document Source, XDS Document Repository, "ATNA-ITI-19"> precedes <XDS Document Source, XDS Document Repository, "XDS-ITI-15">'; it follows that the ATNA-ITI-19 312 transaction must precede XDS-ITI-15 transaction 212 and hence the labels on the integrated profiles graph 350 are adjusted as shown in FIG. 6B. In particular, the sequence number of XDS-ITI-15 transaction 212 is changed from "1" to "2" and the sequence number of XDS-ITI-14 transaction 214 is changed from "2" to "3." Thus, the ATNA-ITI-19 transaction 312 is performed first, the XDS-ITI-15 transaction 212 is performed second and the XDS-ITI-14 transaction is performed third.

In one example, an IHE Actor Grouping Tool (IHE-AGT) to perform process 100 is formed using JAVA Programming Language (version 1.5.0) and the installation of the IHE-AGT tool is realized with Jakarta Ant project build tool. In one example, the IHE-AGT produces the integrated profiles graph 350.

Figure 7:
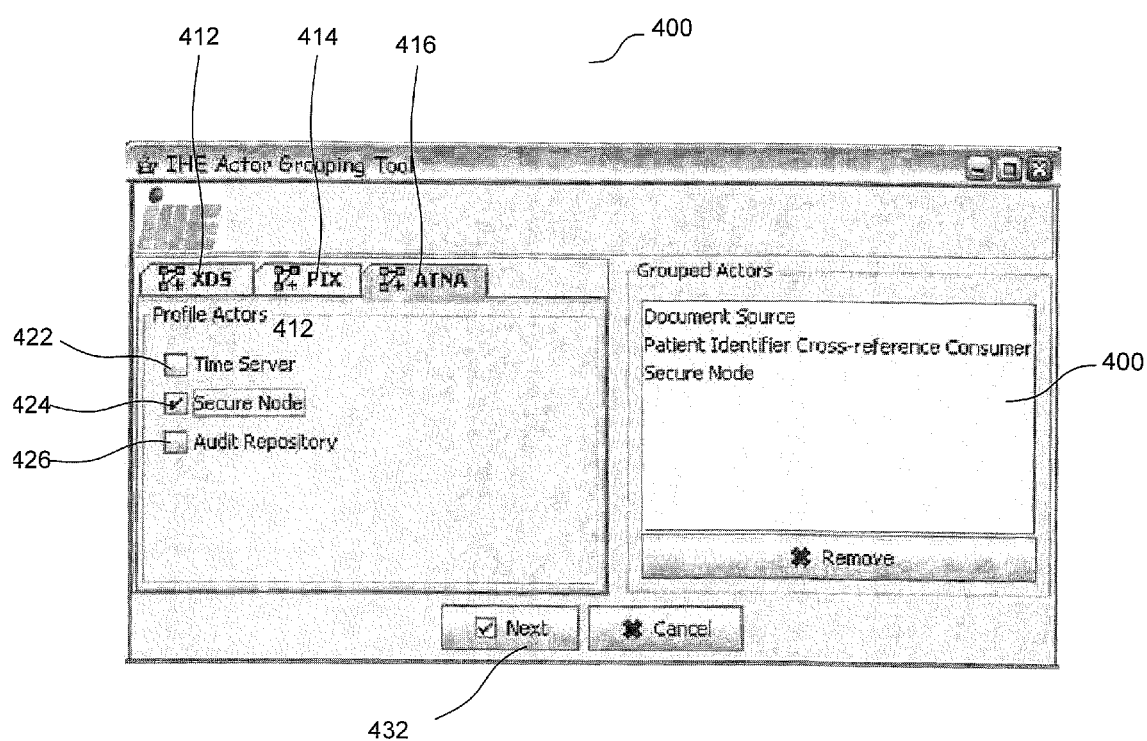
FIGS. 7 and 8 are examples of screenshots for a tool to group actors of different profiles.

FIG. 7 shows an example of a screenshot 400 used in the IHE Actor Grouping Tool where the IHE-XDS Document Source, an IHE-PIX Patient Identifier Cross-reference Consumer and the IHE-ATNA Secure Node are shown grouped in a field 202. The user may select the actors by profile by selecting tabs. For example, an XDS tab 412 allows a user to pick XDS-type actors, a PIX tab 414 allows a user to pick PIX-type actors and an ATNA tab 416 allows a user to select ATNA-type actors. Each tab includes checkboxes to select the actors to group. For example, the ATNA tab 416 includes a timer server check box 422 to select a time server, a secure node checkbox 424 to select a secure node and an audit repository checkbox 426 to select the audit repository. The screenshot 400 also includes a Next button 432 to display IHE transactions in the profiles.

Figure 8:
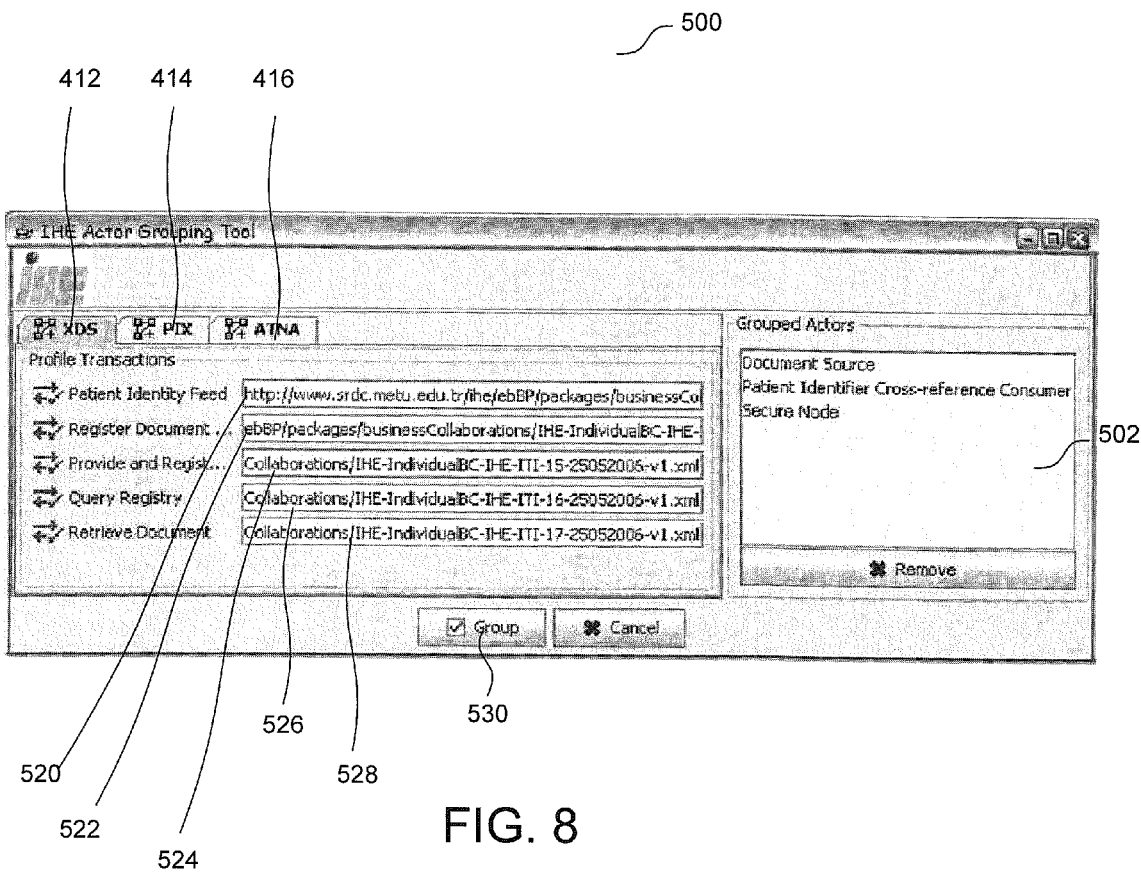

Referring to FIG. 8, after pressing the Next button 432 (FIG. 7), the grouped actors are displayed in field 502 and the IHE transactions for each profile are displayed as shown in a screenshot 500. In one example, the user may select profile transactions using a XDS tab 412 to access XDS transactions, a PIX tab 414 to access PIX transactions and an ATNA tab 416 to access ATNA transactions. In one example, the user may enter URLs of corresponding ebBP Business Collaboration definitions. For example, a user may use a text box 520 to enter a definition for patient identity feed transaction 22, a text box 522 to enter a definition for the register document transaction 26, a text box 524 to enter a definition for the provide & register transaction 24, a text box 526 to enter a definition for the query registry transaction 28 and a text box 528 to enter a definition for the retrieve document transaction 30. The user presses a Group button 530 in order to generate the overall business process definition.

The IHE-AGT tool has an extensible architecture because the IHE profiles are being specified continuously. As new profiles emerge, they can be incorporated into the IHE-AGT tool easily by editing the configuration files. The IHE-AGT tool includes the following information in its configuration files: names of the IHE Actors, names of the IHE Transactions along with the URL references to the corresponding Business Collaboration definitions in ebBP and the precedence rules such as rules for grouping Actors within an IHE Profile and rules for grouping Actors across IHE Profiles.

Figure 9:
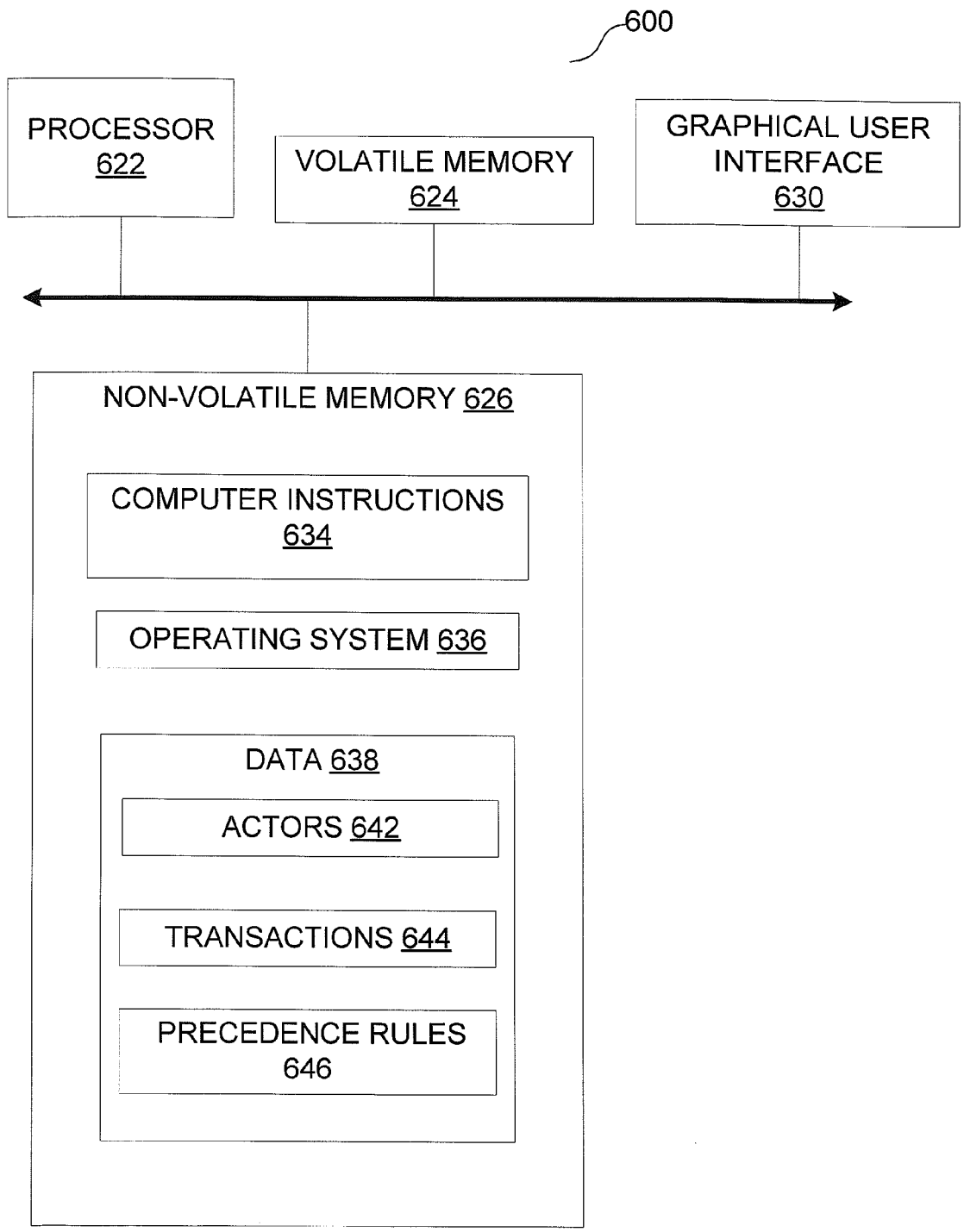
FIG. 9 is a block diagram of an example of a computer on which the process of FIG. 4 may be implemented.

FIG. 9 is an example of a computer 600, which may be used to execute all or part of the process 100. Computer 600 includes a processor 622, a volatile memory 624, a non-volatile memory 626 (e.g., hard disk), for example, and a graphical user interface 630 (e.g., a screen, a mouse, a keyboard, a touch screen and so forth and any combination thereof). Non-volatile memory 626 includes an operating system 636; data 638 (including actors 642, transactions 644 and precedence rules 646); and computer instructions 634 which are executed out of volatile memory 624 to perform all or part of process 100.

The processes described herein (e.g., process 100) are not limited to use with the hardware and software of FIG. 9; they may find applicability in any computing or processing environment and with any type of machine or set of machines that is capable of running a computer program. The processes may be implemented in hardware, software, or a combination of the two. The processes may be implemented in computer programs executed on programmable computers/machines that each includes a processor, a storage medium or other article of manufacture that is readable by the processor (including volatile and non-volatile memory and/or storage elements), at least one input device, and one or more output devices. Program code may be applied to data entered using an input device to perform process 100, for example, and to generate output information.

The processes described herein are not limited to the specific embodiments described herein. For example, the processes are not limited to the specific processing order of the process steps in FIG. 4. Rather, any of the processing steps of FIG. 4 may be re-ordered, combined or removed, performed in parallel or in serial, as necessary, to achieve the results set forth above. The processes are not limited to IHE profiles. For example, the process can be applied to HL7 v3 storyboards, a messaging standard in the eHealth domain.

Figure 4:
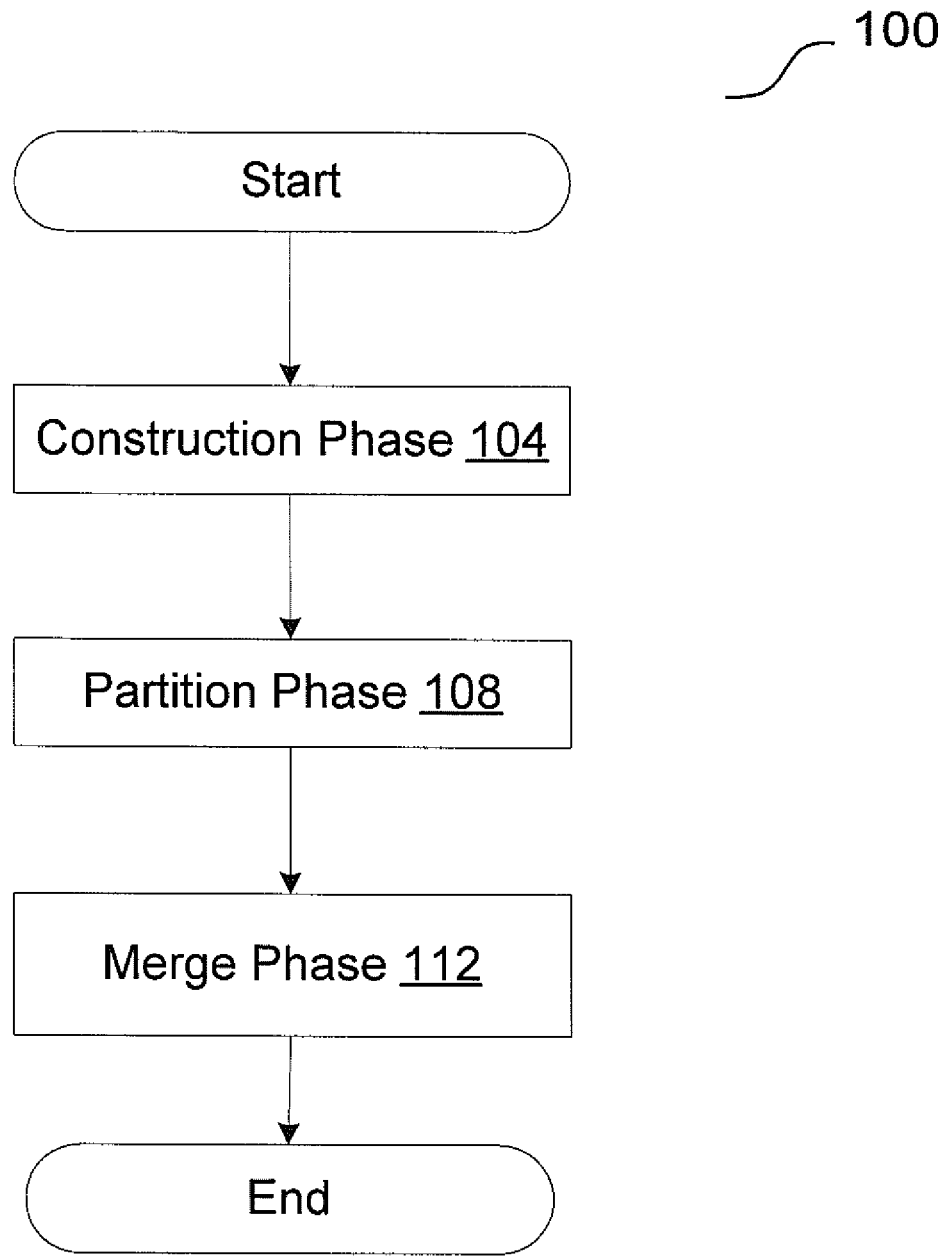
FIG. 4 is an example of a flowchart to group actors of different profiles.

Process steps in FIG. 4 associated with implementing the system may be performed by one or more programmable processors executing one or more computer programs to perform the functions of the system. All or part of the system may be implemented as, special purpose logic circuitry (e.g., an FPGA (field programmable gate array) and/or an ASIC (application-specific integrated circuit)).

While the invention is shown and described in conjunction with a particular embodiment having an illustrative architecture having certain components in a given order, it is understood that other embodiments well within the scope of the invention are contemplated having more and fewer components, having different types of components, and being coupled in various arrangements. Such embodiments will be readily apparent to one of ordinary skill in the art. All documents cited herein are incorporated herein by reference. Other embodiments not specifically described herein are also within the scope of the following claims.

What is claimed is:

1. A method to integrate different profiles to form a process, comprising:
    providing, to a user using a graphical user interface (GUI) of a computer system, a list of actors by Integrating Healthcare Enterprise (IHE) profile, an actor comprising one of a system or an application stored on a non-transitory machine-readable medium;
    providing, to the user through the GUI, a list of IHE transactions by IHE profile performed by the actors;
    receiving, from the user using the GUI, a selection of actors from the list of actors by IHE profile to group, the selection of actors comprising actors from different IHE profiles;
    receiving, from the user using the GUI, definitions of the IHE transactions;
    grouping, using the computer system, the selection of actors based on at least precedence rules indicating an order IHE transactions are performed and comprising rules for grouping actors within an IHE profile and rules for grouping actors across different IHE profiles; and
    rendering, by using the GUI of the computer system, to the user an integrated profiles graph representing the grouping of the selection of actors from different IHE profiles.

2. The method of claim 1 wherein providing to a user a list of actors by profile comprises providing to a user a list of actors from at least two of an Integrating Healthcare Enterprise (IHE) Cross-Enterprise Document Sharing (IHE-XDS) Profile; an IHE Audit Trail and Node Authentication (ATNA) Integration Profile and a Patient Identifier Cross-referencing Integration (IHE-PIX) Profile.

3. The method of claim 2 wherein providing to a user a list of transactions by profile comprises providing to a user a list of transactions by profile from at least two of the IHE-XDS Profile; the ATNA Profile and the IHE-PIX Profile.

4. The method of claim 1, further comprising:
    generating an overall process graph comprising:
        nodes representing the actors; and
        vertices representing the transactions, the transactions comprising a sequence number indicating order of execution.

5. The method of claim 4 wherein grouping the selection of actors based on precedence rules comprises:
    partitioning the overall process graph into subgraphs;
    merging at least two of the nodes in a subgraph; and
    reordering at least one of the transactions in the subgraph based on the precedence rules.

6. An article comprising:
    a non-transitory machine-readable medium that stores executable instructions to integrate different profiles to form a process, the instructions causing a machine to:
        provide, to a user using a graphical user interface (GUI) of a computer system, a list of actors by Integrating Healthcare Enterprise (IHE) profile, an actor comprising one of a system or an application;
        provide, to the user through the GUI, a list of IHE transactions by IHE profile performed by the actors;
        receive, from the user using the GUI, a selection of actors from the list of actors by IHE profile to group, the selection of actors comprising actors from different IHE profiles;
        receive, from the user using the GUI, definitions of the IHE transactions;
        group the selection of actors based on at least precedence rules indicating an order IHE transactions are performed and comprising rules for grouping actors within an IHE profile and rules for grouping actors across different IHE profiles; and
        render to the user an integrated profiles graph representing the grouping of the selection of actors from different IHE profiles.

7. The article of claim 6 wherein the instructions causing a machine to provide to a user a list of actors by profile comprises instructions causing a machine to provide to a user a list of actors from at least two of an Integrating Healthcare Enterprise (IHE) Cross-Enterprise Document Sharing (IHE-XDS) Profile; an IHE Audit Trail and Node Authentication (ATNA) Integration Profile and a Patient Identifier Cross-referencing Integration (IHE-PIX) Profile.

8. The article of claim 7 wherein the instructions causing a machine to provide to a user a list of transactions by profile comprises instructions causing a machine to provide to a user a list of transactions by profile from at least two of the IHE-XDS Profile; the ATNA Profile and the IHE-PIX Profile.

9. The article of claim 6, further comprising instructions causing a machine to:
    generate an overall process graph comprising:
    nodes representing the actors; and
    vertices representing the transactions, the transactions comprising a sequence number indicating order of execution,
    wherein the instructions causing a machine to group the selection of actors based on precedence rules comprises instructions causing a machine to:
    partition the overall process graph into subgraphs;
    merge at least two of the nodes in a subgraph; and
    reorder at least one of the transactions in the subgraph based on the precedence rules.

10. An apparatus to integrate different profiles to form a process, comprising:
    an electronic hardware circuitry configured to:
        provide, to a user using a graphical user interface (GUI) of a computer system, a list of actors by Integrating Healthcare Enterprise (IHE) profile, an actor comprising one of a system or an application;
        provide, to the user through the GUI, a list of IHE transactions by IHE profile performed by the actors;
        receive, from the user using the GUI, a selection of actors from the list of actors by IHE profile to group, the selection of actors comprising actors from different IHE profiles;
        receive, from the user using the GUI, definitions of the IHE transactions;

group the selection of actors based on at least precedence rules indicating an order IHE transactions are performed and comprising rules for grouping actors within a an IHE profile and rules for grouping actors across different IHE profiles; and
  render to the user an integrated profiles graph representing the grouping of the selection of actors from different IHE profiles.

11. The apparatus of claim 10 wherein the electronic hardware circuitry comprises a processor.

12. The apparatus of claim 10 wherein the electronic hardware circuitry is further configured to provide to a user a list of actors by profile comprises circuitry to provide to a user a list of actors from at least two of an Integrating Healthcare Enterprise (IHE) Cross-Enterprise Document Sharing (IHE-XDS) Profile; an IHE Audit Trail and Node Authentication (ATNA) Integration Profile and a Patient Identifier Cross-referencing Integration (IHE-PIX) Profile.

13. The apparatus of claim 12 wherein the electronic hardware circuitry is further configured to provide to a user a list of transactions by profile comprises circuitry to provide to a user a list of transactions by profile from at least two of the IHE-XDS Profile; the ATNA Profile and the IHE-PIX Profile.

14. The apparatus of claim 10, further comprising the electronic hardware circuitry configured to:
  generate an overall process graph comprising:
  nodes representing the actors; and
  vertices representing the transactions, the transactions comprising a sequence number indicating order of execution,
  wherein the circuitry to group the selection of actors based on precedence rules comprises circuitry to:
  partition the overall process graph into subgraphs; merge at least two of the nodes in a subgraph; and
  reorder at least one of the transactions in the subgraph based on the precedence rules.

* * * * *